United States Patent [19]
Hackler et al.

[11] Patent Number: 6,040,345
[45] Date of Patent: Mar. 21, 2000

[54] BENZOYLPHENYLUREA INSECTICIDES AND METHODS OF USING THEM TO CONTROL COCKROACHES

[75] Inventors: Ronald E. Hackler, Indianapolis; Kathryn E. Lawrence, Crawfordsville, both of Ind.

[73] Assignee: Dow AgroSciences LLC, Indianapolis, Ind.

[21] Appl. No.: 08/962,565

[22] Filed: Oct. 31, 1997

Related U.S. Application Data

[60] Provisional application No. 60/029,748, Nov. 8, 1996.

[51] Int. Cl.⁷ .................................................. A01N 31/17
[52] U.S. Cl. ............................................. 514/594; 564/44
[58] Field of Search .................................. 514/594; 564/44

[56] References Cited

U.S. PATENT DOCUMENTS

| | | | |
|---|---|---|---|
| 3,748,356 | 7/1973 | Wellinga et al. | 260/553 E |
| 4,468,405 | 8/1984 | Rigterink et al. | 424/322 |
| 4,798,837 | 1/1989 | Drabek et al. | 514/594 |
| 4,925,875 | 5/1990 | Drabek | 514/594 |
| 4,925,876 | 5/1990 | Drabek | 514/594 |
| 4,973,589 | 11/1990 | Barnett et al. | 514/245 |
| 5,132,325 | 7/1992 | Drabek et al. | 514/594 |
| 5,153,224 | 10/1992 | Drabek et al. | 574/594 |
| 5,288,756 | 2/1994 | Drabek et al. | 514/594 |
| 5,416,102 | 5/1995 | Barnett et al. | 514/351 |
| 5,556,883 | 9/1996 | Thoms et al. | 514/594 |

FOREIGN PATENT DOCUMENTS

| | | |
|---|---|---|
| 68094/87 | 8/1987 | Australia . |
| 87/71748 | 10/1987 | Australia . |
| 194688 | 9/1986 | European Pat. Off. . |
| 221847 A2 | 5/1987 | European Pat. Off. . |
| 0243790 A1 | 11/1987 | European Pat. Off. . |
| 263438 A2 | 4/1988 | European Pat. Off. . |
| 290392 A1 | 11/1988 | European Pat. Off. . |
| 3827133 A1 | 2/1989 | Germany . |
| 2166134 | 4/1986 | United Kingdom . |
| WO 94/03066 | 2/1994 | WIPO . |
| WO 95/16354 | 6/1995 | WIPO . |

OTHER PUBLICATIONS

Journal of Economic Entomology (Oct., 1996), vol. 89, No. 5, pp. 1156–1160, Nan–Yao Su and Rudolf H. Scheffrahn, "Comparative Effects of Two Chitin Synthesis Inhibitors, Hexaflumuron and Lufenuron, in a Bait Matrix Against Subterranean Termites (*Isoptera:Rhinotermitidae*)".

*Primary Examiner*—Peter O'Sullivan
*Attorney, Agent, or Firm*—Carl D. Corvin; Donald R. Stuart

[57] ABSTRACT

Compounds of formula (I):

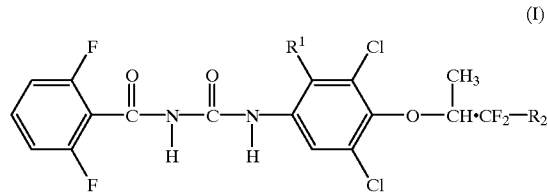

wherein $R^1$ is H or F and $R^2$ is $CF_3$ or $CF_2CF_3$, exhibit unexpectedly superior activity against cockroaches and are also useful to control other insects.

8 Claims, No Drawings

BENZOYLPHENYLUREA INSECTICIDES AND METHODS OF USING THEM TO CONTROL COCKROACHES

CROSS REFERENCE RELATED APPLICATION

This patent application claims the benefit of Provisional U.S. patent application Ser. No. 60/029,748 filed Nov. 8, 1996.

BACKGROUND OF THE INVENTION

This invention provides novel benzoylphenylurea inseciticides and novel methods of inhibiting cockroaches.

A broad class of benzoylphenylurea insecticides is disclosed in U.S. Pat. No. 3,748,356. Hexaflumuron, a commercially significant benzoylphenylurea, is disclosed in U.S. Pat. No. 4,468,405. Use of hexaflumuron to control cockroaches is disclosed in WO 94/03066.

We have discovered that certain novel benzoylpheylureas have substantially greater activity against cockroaches than would have been expected based on comparison with the closest prior art, i.e. hexaflumuron. The novel compounds can also be used to control other insects, such as ants, fleas, and termites.

SUMMARY OF THE INVENTION

The invention provides new compounds of formula (I):

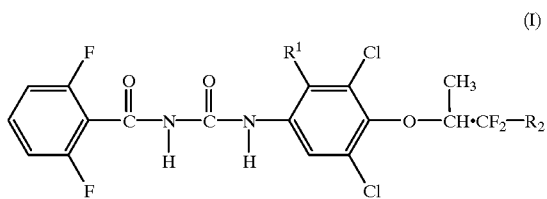

wherein $R^1$ is H or F and $R^2$ is $CF_3$ or $CF_2CF_3$.

The invention also provides a method of controlling cockroaches which comprises delivering an effective amount of a compound of the formula (I) to a location where control of cockroaches is desired.

The invention also provides a method of controlling insects which comprises delivering an effective amount of a compound of formula (I) to a location where control of insects is desired.

DETAILED DESCRIPTION OF THE INVENTION

Intermediate 1: 2,6-difluorobenzoyl isocyanate

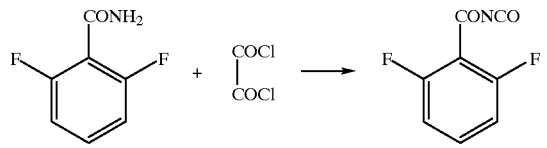

A mixture of 0.52 g of 2,6-difluorobenzamide and 0.33 ml of oxalyl chloride was stirred under reflux in 15 ml 1,2-dichloroethane overnight. Solvent was removed under vacuum and 10 ml 1,2-dichloroethane was added. Solvent was removed under vacuum to leave the title intermediate, which could be used directly or dissolved in 1,2-dichloroethane and stored for future use.

Intermediate 2: 3,5-Dichloro-4-(1-methyl-2,2,3,3,3-pentafluoropropoxy)aniline

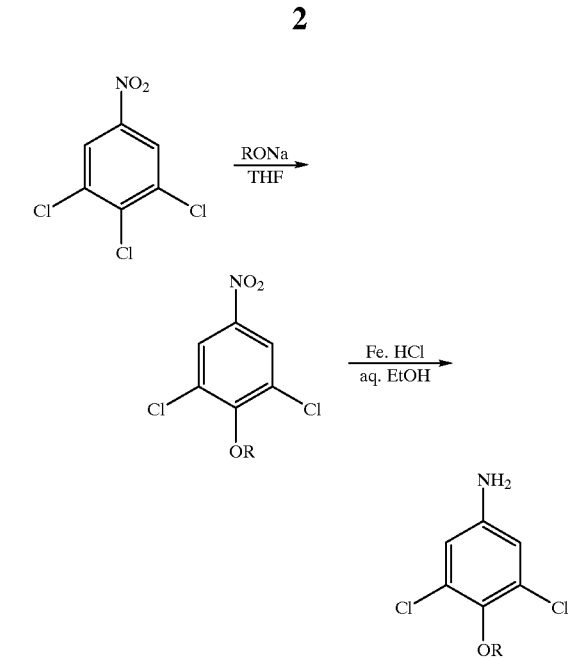

A. 1.1 g sodium hydride (60% in oil) was washed with hexanes and 25 mL THF was added. 3.0 g 1-methyl-2,2,3,3,3-pentafluoropropanol was diluted in 5 mL THF and added dropwise to the mixture. Then 4.1 g of 3,4,5-trichloronitrobenzene was added in 15 mL THF. The mixture was heated under reflux for 10 hrs. TLC showed reaction to be complete and the mixture was poured onto 125 mL ice water and extracted with 4×100 mL portions diethyl ether. The combined organics were washed with brine and water before drying ($MgSO_4$), filtering, and concentrating in vacuo to give 5.63 g of 3,5-dichloro-4-(1-methyl-2,2,3,3,3-pentafluoropropoxy)nitrobenzene as an amber oil. $^1$H: 8.25 (s, 2H), 5.24 (m, 1H), 1.50 (d, J=6.61 Hz, 3H). MS: 353 m/z. IR: 1537(s), 1348(s) $cm^{-1}$. Anal. Calcd $C_{10}H_6Cl_2F_5NO_3$: C, 33.92; H, 1.71; N, 3.96. Found: C, 35.42; H, 1.94; N, 4.26.

B. 4.0 g iron filings, 240 mL of a 2/1 ethanol-water mixture, and 4.86 g 3,5-dichloro-4-(1-methyl-2,2,3,3,3-pentafluoropropoxy)nitrobenzene was stirred vigorously and heated under reflux while 1.0 mL conc. HCl in 2 mL ethanol was added dropwise. After one hour 2.0 mL conc. HCl in 2.0 mL ethanol was added and reflux was maintained overnight (about 15 hours). The mixture was filtered hot through Celite. The filtrate was concentrated under vacuum before being partitioned in saturated sodium bicarbonate and diethyl ether. The layers were separated and the aqueous layer was extracted with diethyl ether. The combined organics were washed with brine, dried ($MgSO_4$), filtered, and concentrated to give 3.86 g of 3,5-Dichloro-4-(1-methyl-2,2,3,3,3-pentafluoropropoxy)aniline as an amber oil. $^1$H NMR and GC/MS confirm pure product. Anal. calcd $C_{10}H_8Cl_2F_5NO$: C, 37.06; H, 2.49; N, 4.32. Found: C, 38.71; H, 2.51; N, 4.65.

Intermediate 3: 3,5-Dichloro-4-(1-methyl-2,2,3,3,4,4,4-heptafluorobutoxy)aniline A. 1.4 g sodium hydride (60% in oil) was washed with hexanes and 30 mL THF was added. 5.0 g 1-methyl-2,2,3,3,4,4,4-heptafluorobutanol was diluted in 5 mL THF and added dropwise to the mixture. Then 5.3 g of 3,4,5-trichloronitrobenzene was added in 10 mL THF. The mixture was heated under reflux overnight. TLC showed reaction to be complete and the mixture was poured onto 200 mL ice water and extracted with 5×125 mL portions diethyl ether. The combined organics were washed with brine and water before drying (MgSO$_4$), filtering, and concentrating in vacuo to give 8.41 g of 3,5-Dichloro-4-(1-methyl-2,2,3,3,4,4,4-heptafluorobutoxy)nitrobenzene as an amber solid.

$^1$H: 8.24 (s, 2H), 5.33 (m, 1H), 1.45 d, J=6.0 Hz, 3H). MS: 403 m/z. IR: 1537(s), 1348(s) cm$^{-1}$.

B. 5.29 g iron filings, 240 mL of a 2/1 ethanol-water mixture, and 8.3 g 3,5-dichloro-4-(1-methyl-2,2,3,3,4,4,4-heptafluorobutoxy)nitrobenzene was stirred vigorously and heated under reflux while 2.0 mL conc. HCl in 2 mL ethanol was added dropwise. After one hour 2.0 mL conc. HCl in 2.0 mL ethanol was added and reflux was maintained for 6 hrs. Then added 2.0 mL conc. HCl in 3.0 mL ethanol and maintained reflux overnight. The mixture was filtered hot through Celite. The filtrate was concentrated under vacuum before being partitioned in saturated sodium bicarbonate and diethyl ether. The layers were separated and the aqueous layer was extracted with diethyl ether. The combined organics were washed with brine, dried (MgSO$_4$), filtered, and concentrated to give 4.79 g of 3,5-Dichloro-4-(1-methyl-2,2,3,3,4,4,4-heptafluorobutoxy)aniline as an amber oil. $^1$H NMR and MS confirm pure product. Anal. calcd C$_{11}$H$_8$Cl$_2$F$_7$NO: C, 35.32; H, 2.16; N, 3.74. Found: C, 36.40; H, 2.33; N, 3.98.

Intermediate 4: 2-Fluoro-3,5-Dichloro-4-(1-methyl-2,2,3,3,3-pentafluoropropoxy)aniline

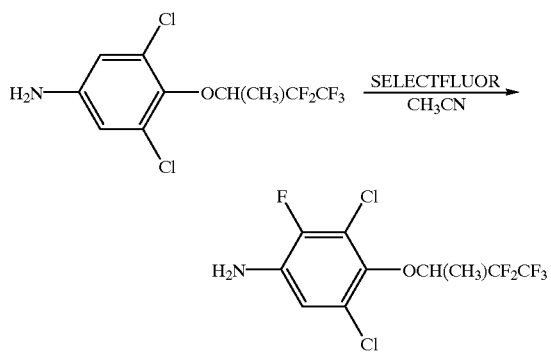

1.0 g 3,5-dichloro-4-(1-methyl-2,2,3,3,3-pentafluoropropoxy)aniline was dissolved in 25 mL acetonitrile under nitrogen atomosphere. Then 1.04 g of Selectfluor® (F-TEDA) was added in a few small portions at once. The mixture was heated to near reflux for 3 hours. The mixture was cooled to room temperature and quenched with 80 mL saturated NaHCO$_3$ solution. Ethyl acetate (3×75 mL) was used to extract the mixture. The combined organics were washed with brine, dried (MgSO$_4$), filtered, and concentrated to give 1.22 g crude product. Purified on silica gel using 10% ethyl acetate/hexane to give 220 mg product as an amber oil. $^1$H NMR and MS confirm structure.

Compound 1: 1-(2,6-Difluorobenzoyl)-3-[3.5-dichloro-4-(1-methyl-2,2,3,3,3-pentafluoropropoxy)phenyl]urea

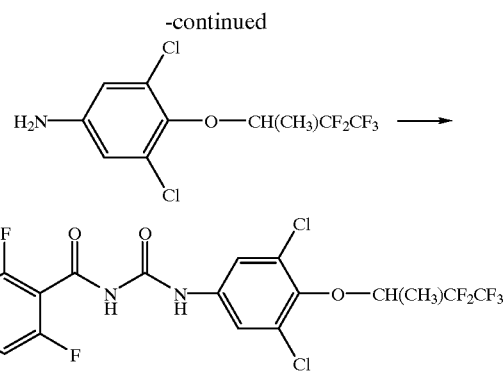

1.0 of 3,5-Dichloro-4-(1-methyl-2,2,3,3,3-pentafluoropropoxy)aniline was placed in a flask to which was added 15 mL of 1,2-dichloroethane. With stirring, 0.62 g 2.6-difluorobenzoyl isocyanate was added all at once to the mixture. The mixture was warmed to near reflux for one hour then cooled to room temperature and stirred overnight. It was then concentrated under vacuum to give 2.30 g crude product. The product was recrystallized from toluene, giving 208 mg of 1-(2,6-difluorobenzoyl)-3-[3,5-dichloro-4-(1-methyl-2,2,3,3,3-pentafluoropropoxy)phenyl]urea. $^1$H NMR: 10.59 (s, 1H) 9.58 (s, 1H), 7.34 (m, 3H), 7.07 (t, J=8.4 Hz,2H), 5.09 (m, 1H). MS: 506 m/z. IR:1746(s), 1710(s), 1539(s), 1470(m).

Compound 2: 1-(2,6-Difluorobenzoyl)-3-[2-fluoro-3,5-dichloro-4-(1-methyl-2,2,3,3-,pentafluoroproloxy)phenyl]urea

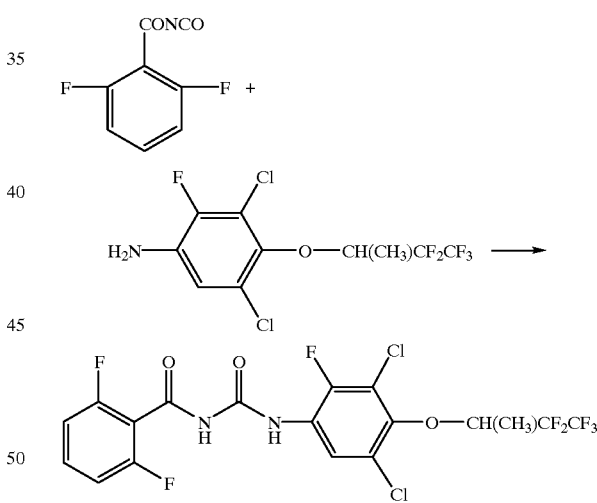

200 mg of 2-Fluoro-3,5-dichloro-4-(1-methyl-2,2,3,3,3-pentafluoropropoxy)aniline was stirred in 15 mL 1,2-dichloroethane as 118 mg 2,6-difluorobenzoyl isocyanate in 5 mL 1,2-dichloroethane was added. The mixture was heated under reflux for 30 minutes before lowering heat and stirring overnight. The mixture was then concentrated to half volume and chilled to give 120 mg of 1-(2,6-Difluorobenzoyl)-3-[2-fluoro-3,5-dichloro-4-(1-methyl-2,2,3,3,3-pentafluoropropoxy)phenyl]urea as a white solid. $^1$H NMR: 10.60 (s, 1H), 9.46 (s, 1H), 8.11 (d, J=8.0 Hz, 1H), 7.54 (m, 1H), 7.08 (t, J=8.7 Hz, 2H), 5.11 (m, 1H), 1.43 (d, J=6.7 Hz, 3H). MS: 524 m/z. IR: 1699(s), 1469(s).

Compound 3: 1-(2,6-Difluorobenzoyl)-3-[3,5-dichloro-4-(1-methyl-2,2,3,3,4,4,4-heptafluorobutoxy)phenyl]urea

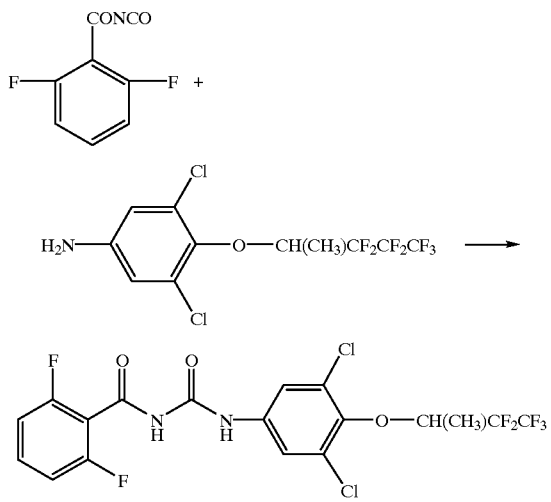

2.0 g 3,5-Dichloro-4-(1-methyl-2,2,3,3,4,4,4-heptafluorobutoxy)aniline was dissolved in 20 mL 1,2-dichloroethane and 1.08 g 2,6-difluorobenzoyl isocyanate in 11 mL 1,2-dichloroethane was added. The mixture was heated near reflux overnight and concentrated under vacuum to about 10 mL. It was then cooled and 0.94 g of 1-(2,6-Difluorobenzoyl)-3-[3,5-dichloro-4-(1-methyl-2,2,3,3,4,4,4-heptafluorobutoxy)phenyl] urea was collected as a white solid. $^1$H NMR confirms structure. $^1$H NMR: 10.57 (s, 1H), 9.36 (s, 1H), 7.54 (m, 3H), 7.07 (t, J=8.4 Hz,2H). MS: 556 m/z. IR: 1711 (s), 1699(s), 1590(s), 1470(s). Anal. Calcd $C_{19}H_{11}Cl_2F_9N_2O_3$: C, 40.96; H, 1.99;, N, 5.03. Found: C, 40.53; H, 1.78; N, 4.88.

Biological Activity

German Cockroach 2nd Instars (*Blattella germanica*)

Continuous, low-dose ingestion exposure (treated cornmeal) Rates: 0.19, 0.78, 3.12, 12.5, 50, and 200 ppm.

| Compound | $LC_{50}$ (ppm) | |
|---|---|---|
| | 21 days | 42 days |
| Compound 1 | 0.77 | 0.24 |
| Compound 2 | 0.9 | <0.19 |
| Compound 3 | 1.6 | 0.22 |
| hexaflumuron | >200 | >200 |

Under continuous exposure, the compounds of Compounds 1–3 are far more active than hexaflumuron.

German Cockroach 2nd Instars (Blattella Germanica)

Limited ingestion exposure (48 hr.) to treated cornmeal. Rates: 1, 10, 100, 1000, 10000 ppm.

| Compound | $LC_{50}$ (ppm) | |
|---|---|---|
| | 21 days | 42 days |
| Compound 1 | 19.2 | 14.0 |
| Compound 2 | <1.0 | <1.0 |
| Compound 3 | 4.5 | 1.7 |
| hexaflumuron | >10,000 | >10,000 |

Under limited exposure, the compounds of Compounds 1–3 were more potent than hexaflumuron at both 21 and 42 days after exposure.

Formulations

When used to control cockroaches, it is preferred to use the active ingredient in a treated diet or as a surface treatment. Suitable formulations include granular, paste, or dust cockroach bait, SP or WP cockroach sprayables.

In order to facilitate the application of the compounds of formula (I) to the desired locus, or to facilitate storage, transport or handling, the compound is normally formulated with a carrier and/or a surface-active agent.

A carrier in the present context is any material with which the compound of formula (I) (active ingredient) is formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar, paper products, cotton linter, or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone; oils derived from plants, such as corn oil and peanut oil. Mixtures of different liquids are often suitable, for example a mixture of isophorone with a polar organic solvent such as N-methylpyrrolidone, as are mixtures of solid and liquid carriers. Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surfaceactive agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide.

Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a suitable food source, such as grain or meal for cockroaches, with an amount of active ingredient sufficient to provide the desired result; for example, from about 0.001% to about 20% weight active ingredient and forming the mixture into a paste by the addition of about 1% to 5% of a water based binder such as agar. The paste-like mixture may be applied as is or may be packed into a housing such as a plastic tube or bait station. In other embodiments, sheets of paper or cardboard can be sprayed with or dipped in a diluted formulation containing the active ingredient. Baits are a preferable embodiment of the present invention.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

We claim:

1. A compound of formula (I):

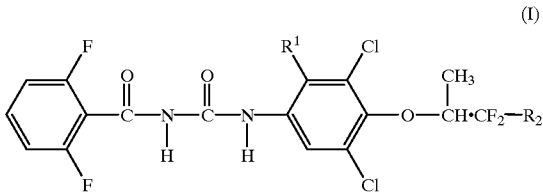

wherein $R^1$ is H or F and $R^2$ is $CF_3$ or $CF_2CF_3$.

2. The compound of claim 1 which is 1-(2,6-Difluorobenzoyl)-3-[3,5-dichloro-4-(1-methyl-2,2,3,3,3-pentafluoropropoxy)phenyl]urea.

3. The compound of claim 1 which is 1-(2,6-Difluorobenzoyl)-3-[2-fluoro-3,5-dichloro-4-(1-methyl-2,2,3,3,3-pentafluoropropoxy)phenyl]urea.

4. The compound of claim 1 which is 1-(2,6-Difluorobenzoyl)-3-[3,5-dichloro-4-(1-methyl-2,2,3,3,4,4,4-heptafluorobutoxy)phenyl]urea.

5. A method of controlling cockroaches which comprises delivering a effective amount of a compound of claim 1 to a location where control of cockroaches is desired.

6. A cockroach bait comprising an effective amount of a compound of claim 1 in combination with a conventional bait matrix.

7. A method of controlling insects which comprises delivering a effective amount of a compound of claim 1 to a location where control of insects is desired.

8. A pesticidal composition comprising an effective amount of a compound of claim 1 in combination with a carrier.

* * * * *